United States Patent [19]

Griffiths

[11] 4,005,116
[45] Jan. 25, 1977

[54] ORGANOSILICON COMPOUNDS

[75] Inventor: Brian John Griffiths, Coytrahen, near Bridgend, Wales

[73] Assignee: Dow Corning Limited, Barry Glamorgan, Wales

[22] Filed: Nov. 6, 1975

[21] Appl. No.: 629,269

[30] Foreign Application Priority Data

Nov. 27, 1974 United Kingdom ............ 49029/74

[52] U.S. Cl. ................ 260/448.2 N; 260/448.8 R; 260/46.5 E; 252/426; 252/431 N

[51] Int. Cl.$^2$ ....................... C07F 7/10; C07F 7/18

[58] Field of Search .............. 260/448.2 N, 448.8 R

[56] References Cited

UNITED STATES PATENTS

| | | | |
|---|---|---|---|
| 3,328,451 | 6/1967 | Bulbenko | 260/448.8 R |
| 3,637,779 | 1/1972 | LeGrow | 260/448.8 R X |
| 3,660,454 | 5/1972 | Gornowicz | 260/448.8 R |
| 3,700,715 | 10/1972 | Berger | 260/448.8 R |

*Primary Examiner*—Paul F. Shaver
*Attorney, Agent, or Firm*—Robert F. Fleming, Jr.

[57] ABSTRACT

Disilazanes having sulphur atoms attached to the silicon atoms through divalent aliphatic hydrocarbon radicals having from 2 to 6 carbon atoms. They are prepared by reacting a disilazane having olefinically unsaturated hydrocarbon radicals attached to the silicon atoms with a thiol, in the presence of a free radical generator. The disilazanes are useful as intermediates and for the treatment of particulate solids.

5 Claims, No Drawings

ORGANOSILICON COMPOUNDS

This invention relates to novel organosilicon compounds and to a method for the preparation thereof.

According to the invention there are provided disilazanes having the general formula HN(R$_2$SiR'SR'')$_2$ wherein each R represents a monovalent radical having from 1 to 8 carbon atoms and free of aliphatic unsaturation which is a hydrocarbon radical, halogenated hydrocarbon radical or hydrocarbonoxy radical, R' represents a divalent aliphatic hydrocarbon radical having from 2 to 6 inclusive carbon atoms and R'' represents a monovalent hydrocarbon radical free of aliphatic unsaturation and having from 1 to 8 inclusive carbon atoms.

In the general formula of the compounds of this invention the R substituents may be the same or different and each R may be, for example, methyl, ethyl, propyl, butyl, 2,4,4-trimethylpentyl, chloromethyl, 3,3,3-trifluoropropyl, cyclohexyl, phenyl, tolyl, methoxy, ethoxy, propoxy, n-butoxy or methoxyethoxy. The divalent radical R' may be, for example —(CH$_2$)$_2$—, $$-CH_2\overset{\overset{\displaystyle CH_3}{|}}{C}HCH_2-$$

or —(CH$_2$)$_4$— and R'' may be, for example, methyl, ethyl, propyl, n-butyl, n-octyl, cyclohexyl and phenyl. Preferably R is methyl or phenyl and R' has from 2 to 4 inclusive carbon atoms.

The compounds of this invention may be prepared by a process which comprises reacting (a) a disilazane of the general formula HN(R$_2$SiR''')$_2$ in which R is as hereinbefore defined and R''' represents a monovalent hydrocarbon radical having from 2 to 6 inclusive carbon atoms and containing olefinic unsaturation, and (b) a thiol R''SH, wherein R'' is as hereinbefore defined, said reaction being carried out in the presence of a free radical initiator.

In the general formula of reactant (a) the substituent R''' may be for example vinyl, allyl or methallyl. Preferably R''' is vinyl or the olefinic unsaturation is present in a terminal position. Reactant (b) may be any thiol conforming to the general formula R''SH, e.g. ethanethiol, butanethiol and octanethiol.

The reaction between (a) and (b) as described above is carried out in the presence of a free radical initiator whereby addition of the thiol to the unsaturation in R''' takes place. Examples of free radical initiators which may be employed are dicumyl peroxide, benzoyl peroxide, t-butyl perbenzoate, azo-bisisobutyronitrile and ultra-violet light. The reaction is exothermic and is preferably carried out in the presence of an organic solvent, for example, toluene, xylene or benzene. Conveniently the reaction is performed at reflux temperature, e.g. from about 60°–120° C but lower temperatures may be employed if desired.

The compounds of this invention are useful as intermediates in the preparation of other sulphur-containing organosilicon products. For example they may be converted by hydrolysis to the silanols and thence by condensation of the silanols to the disiloxanes. They may also be cohydrolysed with other hydrolysable organosilicon compounds to form sulphur-containing organopolysiloxanes. The disilazanes of this invention can be used for the treatment of powders and are especially useful for preparing catalyst carrier substrates as described in our copending application No. 49028/74.

The following example, in which Me represents the methyl radical, illustrates the invention.

EXAMPLE

Sodium-dried A.R. benzene (70 g.) and azo-bisisobutyronitrile (3.3 g.) were placed in a flask and maintained under a blanket of nitrogen at approximately 80° C. Ethanethiol (74.5 g.) and HN(SiMe$_2$CH=CH$_2$)$_2$(92.5 g.) were then added to the contents of the flask from separate dropping funnels. An exothermic reaction occurred and the rate of addition of the reactants was adjusted to maintain the reaction temperature within the range from 70 to 100° C. Addition of the reactants was completed in 50 minutes, after which time heat was supplied to maintain the reaction temperature at about 100° C for a further 1.5 hours.

Distillation of the reaction mixture at 134°–136° C (1.2 mm. Hg.) yielded HN[SiMe$_2$(CH$_2$)$_2$SC$_2$H$_5$]$_2$ (65%). (Found: S, 20.7; C$_{12}$H$_{31}$NSi$_2$S$_2$ requires S, 20.7%).

That which is claimed is:

1. Disilazanes having the general formula

HN(R$_2$SiR'SR'')$_2$ wherein each R represents a monovalent radical having from 1 to 8 carbon atoms and free of aliphatic unsaturation which is a hydrocarbon radical, halogenated hydrocarbon radical or hydrocarbonoxy radical, R' represents a divalent aliphatic hydrocarbon radical having from 2 to 6 inclusive carbon atoms and R'' represents a monovalent hydrocarbon radical free of aliphatic unsaturation and having from 1 to 8 inclusive carbon atoms.

2. Disilazanes as claimed in claim 1 wherein each R is a methyl radical or a phenyl radical.

3. Disilazanes as claimed in claim 1 wherein R' has from 2 to 4 inclusive carbon atoms.

4. A process for the preparation of a disilazane which comprises reacting in the presence of a free radical initiator (a) a disilazane having the general formula HN(R$_2$SiR''')$_2$ in which R is as defined in claim 1 and R''' represents a monovalent hydrocarbon radical having from 2 to 6 carbon atoms and containing olefinic unsaturation, and (b) a thiol R''SH wherein R'' is as defined in claim 1.

5. A process as claimed in claim 4 wherein R''' represents the vinyl radical.

* * * * *